United States Patent [19]

James

[11] Patent Number: 4,563,781
[45] Date of Patent: Jan. 14, 1986

[54] BATH INSTALLATIONS AND BATH TUBS

[75] Inventor: David R. James, Tirley, United Kingdom

[73] Assignee: James Industries Limited, Gloucester, United Kingdom

[21] Appl. No.: 687,945

[22] Filed: Dec. 31, 1984

[30] Foreign Application Priority Data

Jan. 14, 1984 [GB] United Kingdom ............... 8400995

[51] Int. Cl.$^4$ ............................................. A61H 33/02
[52] U.S. Cl. ......................................... 4/542; 4/538;
4/544; 4/222; 4/DIG. 9; 134/24; 134/22.12; 134/166 C
[58] Field of Search ........................ 4/538, 541–544,
4/559, 567–570, 490, DIG. 9, 220, 661, 222,
584, 662; 134/22.12–22.14, 8, 24, 34, 104, 166
C, 167 C, 171; 137/15, 240, 245; 128/65, 66;
239/104, 106

[56] References Cited

U.S. PATENT DOCUMENTS

| | | | |
|---|---|---|---|
| 1,521,697 | 1/1925 | Marschner | 134/166 C |
| 1,628,530 | 5/1927 | Burnett | 134/22.12 |
| 3,080,265 | 3/1963 | Maasberg | 134/24 |
| 3,403,993 | 10/1968 | Hoff | 134/24 |
| 3,493,323 | 2/1970 | Demuth | 134/24 |
| 3,943,580 | 3/1976 | Carter | 4/542 |
| 4,061,571 | 12/1977 | Banner | 134/166 C |
| 4,383,341 | 5/1983 | Altman | 4/538 |

Primary Examiner—Stephen Marcus
Assistant Examiner—Linda J. Sholl
Attorney, Agent, or Firm—Collard, Roe & Galgano

[57] ABSTRACT

A method of disinfecting the circulating system of a whirlpool bath tub installation comprising blanking off or capping a nozzle or nozzles of the bath tub in such manner that a circulating pump and the nozzle(s) together with associated pipework form a closed path. A small supply of disinfecting solution is connected through a valve to the closed path around which the disinfectant solution is circulated by the pump during a disinfection period in order to disinfect the pump, nozzle(s) and associated pipework. A whirlpool bath tub which incorporates a nozzle or nozzles which can be blanked off or capped, thereby providing a closed path and allowing disinfection thereof, by the foregoing method. A whirlpool bath tub installation comprises a tub, nozzles which can be capped, and a disinfectant supply tank. The valve is operable either to connect the pump to circulate water from the tub through the nozzles to which air is fed in the usual manner during bathing or, with the nozzles capped, to circulate disinfectant solution in a closed path which includes the supply tank, nozzles and associated pipework.

17 Claims, 4 Drawing Figures

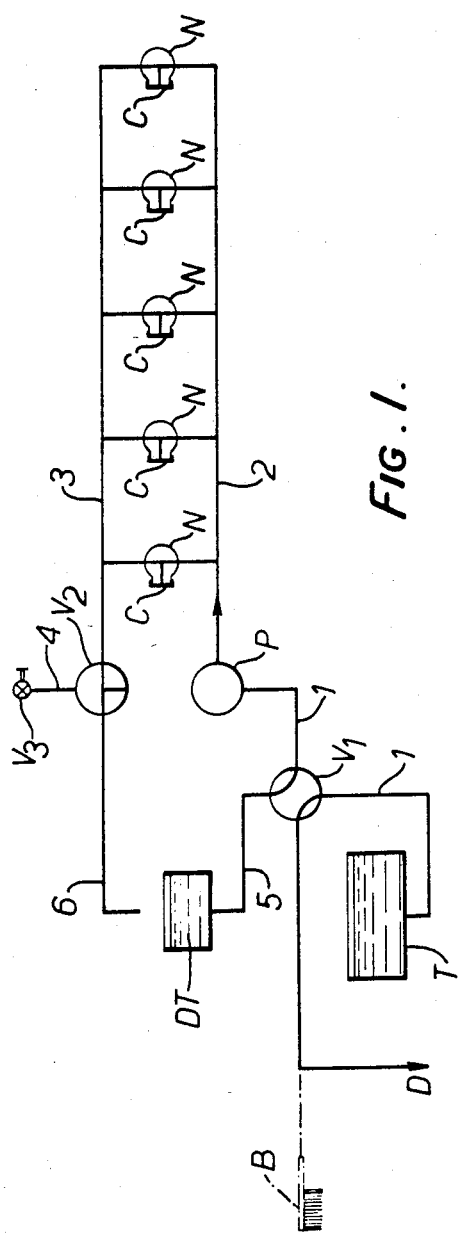
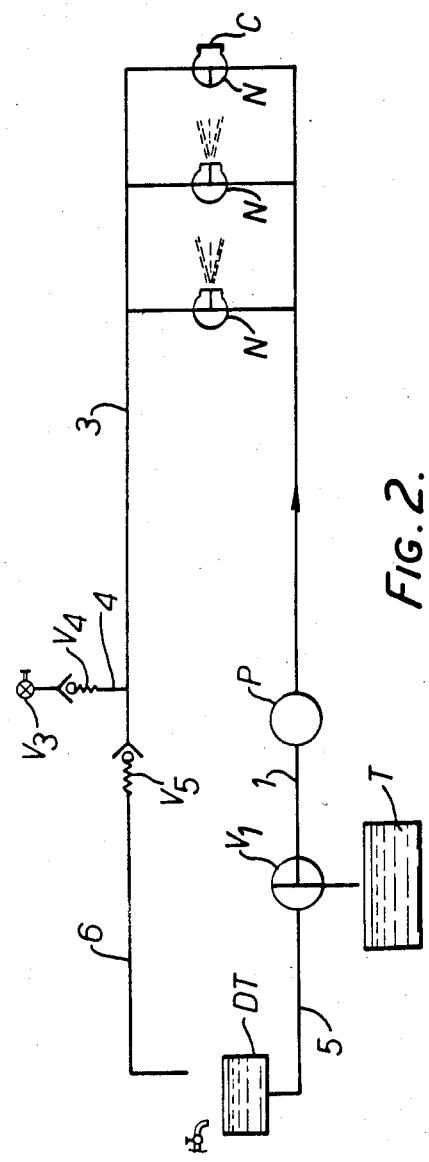

BATH INSTALLATIONS AND BATH TUBS

BACKGROUND OF THE INVENTION

1. Field of the Invention

This invention relates to bath installations including a so-called "whirlpool" bath tub. Such bath tubs are in common use for therapeutic purposes and have at least one nozzle through which the bath water is recirculated by a pump and which emits a pressurized jet of water, in which air bubbles are entrained, into the bathing space. The invention is concerned with such installations and also with bath tubs for use therein.

2. Description of Prior Art

A whirlpool bath tub normally has a plurality of nozzles, commonly three or more, connected in parallel to the pressure outlet of the circulating pump, each nozzle being associated with an air pipe leading to atmosphere and the nozzle constructed so that the air is entrained by means of an injector or venturi action.

In order to prevent cross infection, the whirlpool tubs used in hospitals require that the water circulation path, comprising the nozzles, circulating pumps and associated pipework, should be disinfected between patients. At present this is accomplished by filling the bath with clean water and adding thereto an appropriate disinfectant concentrate to provide a disinfectant solution of adequate strength which is then circulated for an appropriate period. This is an expensive procedure, not only because it requires a considerable quantity of an expensive disinfectant such as iodoform but also in terms of the nursing personnel time involved in filling and refilling the bath which is additional to the recirculation time. Furthermore, the present procedure does not disinfect the air supply system which may on occasion become contaminated, at least in the vicinity of the nozzles, and thus become a source of infection.

SUMMARY OF THE INVENTION

The object of the invention is to provide a method of disinfecting the water circulating system of a whirlpool bath tub, and a bath installation or bath tub designed for disinfection by this method, which is a considerably cheaper procedure in terms of both disinfectant cost and nursing personnel time. A subsidiary object is to provide such a method, installation or bath tub which can if desired be designed for disinfection of the air supply system associated with the nozzles.

According to the invention a method of disinfecting the circulating system of a whirlpool bath tub comprises blanking off or capping the nozzle(s) thereof in such manner that the circulating pump and the nozzle(s) together with associated pipework form a closed path, or a series/parallel closed path arrangement, connecting a small supply of disinfectant solution to said closed path and circulating the disinfectant solution therearound during a disinfection period in order to disinfect the pump, nozzle(s) and associated pipework. As the quantity of disinfectant solution need only be sufficient to fill the closed circulating path a comparatively small volume, say of 5 liters or less, will suffice for a disinfection procedure, after which clean water is circulated to purge the system of the disinfectant.

The closed path may include air supply pipework associated with the nozzle(s), so the such pipework and air channels or ports in the nozzle(s) are simultaneously disinfected. At the end of the disinfection period the used disinfectant may be discharged to drain or, if desired, into the tub itself for disinfection of the latter. Thus it may be discharged through a flexible hose to a hand-held brush for use in cleaning out the bath.

A whirlpool bath tub according to the invention incorporates a nozzle or nozzles and has means for blanking off or capping the or each nozzle of the bath tub, whereby to provide said closed path or path arrangement to allow disinfection thereof by the method of the invention.

The bath tub may have, adjacent the or each nozzle, an outlet connectable to the suction inlet of the pump through which in use and during bathing the recirculated water is drawn by the pump, and in this case the capping means may serve to blank off the or each nozzle and the associated outlet from the inner space of the bath tub in such manner that during the disinfection procedure the disinfectant solution circulated through that nozzle returns through the associated outlet. Alternatively the capping means may blank off the or each nozzle in such a manner that the recirculated disinfectant solution is returned from that nozzle through the air supply pipework associated with the nozzle and in this case the capping means conveniently comprise a capping member which closely fits the end of the nozzle. Such a capping member may be a clip-on, screw-on or plug-in fit to the associated nozzle. Alternatively, the means for blanking off the nozzles may be integral with the respective nozzle assemblies.

According to a more specific aspect of the invention the latter provides the combination of a nozzle for fitting to a whirlpool bath tub and blanking off or capping means which, when fitted, seal off the end of the nozzle with respect to the internal space of the bath tub whereby to allow disinfection in accordance with the method of the invention.

Other features of the invention will be apparent from the following description, drawings and claims, the scope of the invention not being limited to the drawings themselves as the drawings are only for the purpose of illustrating ways in which the principles of the invention can be applied. Other embodiments of the invention utilizing the same or equivalent principles may be made as desired by those skilled in the art without departing from the present invention and the purview of the appended claims.

BRIEF DESCRIPTION OF THE DRAWINGS

FIG. 1 is a diagrammatic flow chart illustrating a whirlpool bath tub installation in accordance with the invention;

FIG. 2 similarly illustrates another such installation;

DESCRIPTION OF THE PREFERRED EMBODIMENTS

Figure 3:
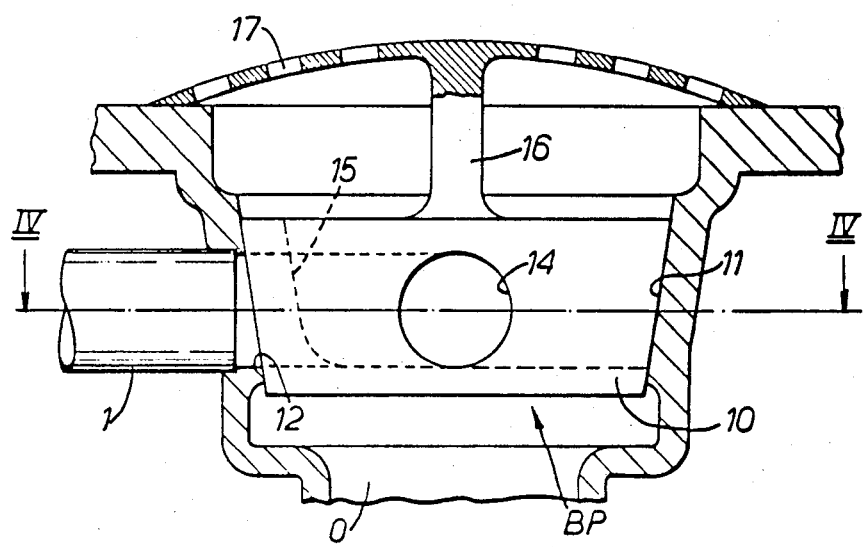
FIG. 3 is a detail view of a modified installation shown in cross-section on a vertical longitudinal plane of the bath tub.

The installation illustrated in FIG. 1 includes a whirlpool bath tub illustrated diagrammatically at T, which is of generally conventional construction and hence not illustrated in detail, with five nozzles N distributed around the wall of the tub so as to discharge into the bathing space. A circulating pump P during the bathing procedure circulates the bath water through the nozzles, and pipework associated with the pump and nozzles comprises a suction pipe 1 connected to the tub and a branched pressure pipe 2 which supplies the individual nozzles N in parallel. Thus the pump P operates to emit a pressurised jet of water from each of the nozzles N which, while passing through the nozzles, entrains air bubbles into jets. The air flow is induced through a branched air supply pipe 3 separately connected to the individual nozzles N and, during bathing, connected to an air inlet pipe 4 which communicates with atmosphere.

The pump supply pipe 1 has fitted therein first valve means comprising a two-position valve V1 which it is connected to the tub T, for recirculation of the water therein, during the bathing procedure. The air supply pipe 3 during this procedure is connected to the air inlet pipe 4 through second valve means comprising a two-position valve V2. In FIG. 1 the valves V1 and V2 are shown in the alternative positions employed in the subsequent disinfection procedure. During that procedure the valve V1 connects the pump inlet to a disinfectant supply pipe 5 leading from a disinfectant supply tank DT, and at this time the valve V2 (as shown) connects the air supply pipe 3 to a disinfectant return pipe 6 which discharges back into the tank DT. During the disinfection procedure each of the nozzels N is individually capped by a suitable capping means C. Such means can be of any convenient form suited to the nozzle construction, for example a snap-on or screw-on molded cap or a push-in closure plug.

With the nozzles N so capped and the valves V1 and V2 in the positions illustrated, operation of the pump for a required disinfection period circulates the disinfectant solution in the tank DT around a closed series/parallel path arrangement which includes the pump P, nozzles N and pipework 1, 2 and 3. The disinfectant entering the nozzles from the pipe 2 leaves them via the pipe 3 through which they are normally supplied with air. Thus the system operates not only to disinfect the parts of the system covered by the presently used and less satisfactory disinfection method but also disinfects the air supply pipework associated with the nozzles N which may have become contaminated.

FIG. 1 illustrates a closure valve V3 at the air inlet of the pipe 4. As a safety measure this can be closed during the disinfection procedure to guard against malfunction or leakage of the valve V2. The valve V1 is positioned close to the tub T so that substantially all of the pipework 1 is included in the closed disinfection path.

The valves V1 and V2 may be manually or automatically operated, in the latter case conveniently providing a timed disinfection cycle. When the valve V1 is in the bathing position it not only connects the pump inlet pipe 1 to the tub T but, as will be clear from the drawing, simultaneously connects the disinfectant supply pipe 5 to drain D and thus disposes of the used disinfectant in the tank DT. For this purpose the valve V1 may be connected directly to drain D or alternatively so as to discharge the contents of the tank DT into the tub T for disinfection of the latter, for example being supplied through a flexible hose to a hand-held brush B (shown in broken lines) provided for cleaning out the tub.

The installation of FIG. 2 operates in a basically similar manner to that of FIG. 1, like reference numerals being used for the two figures where appropriate. In this case the tub is fitted with three nozzles N, for illustrative purposes two of them being shown in the open bathing condition and one capped as in the disinfection procedure. As will be appreciated all three nozzles N are capped during the disinfection procedure when, as before, the valve V1 connects the pump inlet to the tank DT through the pipe 5. In this figure the valve V1 is illustrated in the alternative bathing position in which the pump inlet pipe 1 is connected through the valve V1 to the tub T. Instead of the valve V2 of FIG. 1, the FIG. 2 construction employs second valve means comprising check valves V4 and V5 respectively positioned in the air inlet pipe 4 and the disinfectant return pipe 6. As will be clear from the drawing these check valves are oppositely connected so that they alternately open according to whether or not the nozzles N are capped which, with the pump P operating, determines whether there exists a pressure condition or a suction condition in the air supply pipe 3.

Figure 4:
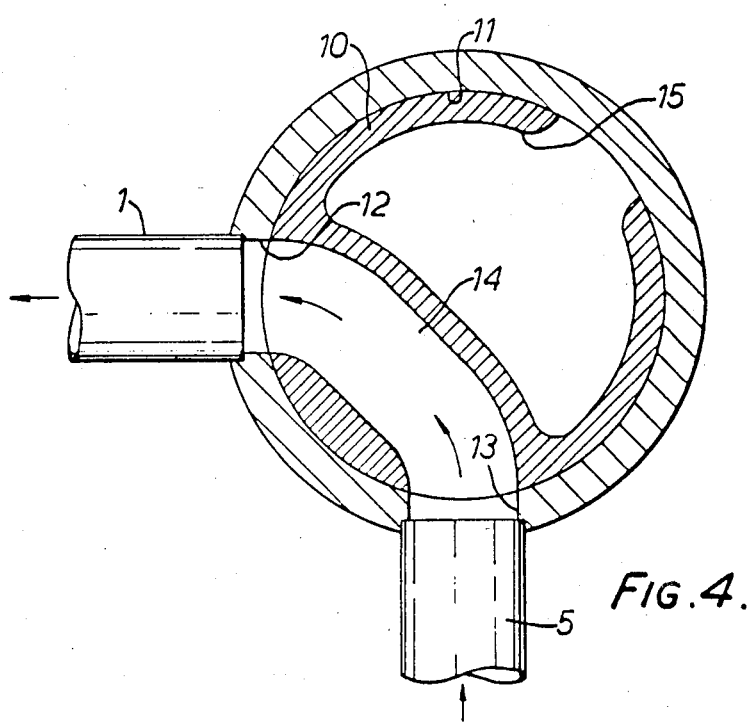
FIG. 4 is a cross-sectional view on the line IV—IV in FIG. 3.

The detail modification shown in FIGS. 3 and 4 modifies the first valve means and in effect combines the valve V1 with the outlet of the tub T, this outlet and the bath plug BP co-operating to provide a two-position 4-way plug valve. The plug BP has a tapered body 10 which fits a taper seating 11 provided by the bath outlet opening O. The pump inlet pipe 1 connected to the valve V1 terminates at a side port 12 in the seat 11, and the disinfectant supply pipe 5 from the tank DT terminates at a side port 13. The valve plug body 10 has a through channel 14 and a cut-away portion 15 which is open at the top and also over a side region of the body 10 so that it communicates above with the inner space of the tub T.

In the angular position of the plug body 10 shown in the drawings the channel 14 interconnects the pipes 1 and 5, to supply the pump P with disinfectant through the valve plug 10 during the disinfection procedure. In an alternative angular position of the plug 10 the bath water is connected to the pipe 1 through the cut-away section 15, so that the pump is supplied from the tub T during the bath procedure.

The angular movement of the closure plug 10 is suitably limited by stops (not shown), which define the alternative plug positions described. The plug body 10 is connected through a central narrow neck 16 with an upper grill section 17 which seats around the tub outlet and is suitably formed to provide a handgrip for manual operation of the plug BP which, at the end of the bathing procedure, is lifted to drain the tub T through the bath outlet O before being replaced in the appropriate angular position for the disinfection procedure.

The bath plug BP may in a further modification be associated with an operating mechanism having an operating handle which projects below the tub T. Alternatively, such mechanism may be automatically operated together with the valve(s) associated with the pipework. An automatic system may provide a control switch, conveniently a pushbutton, actuation of which drains the bath tub and then initiates the disinfection procedure on a timed cycle.

I claim:

1. A method of disinfecting a circulating system of a whirlpool bath tub which comprises at least one nozzle, a circulating pump and associated pipework, said method comprising blanking off or capping the nozzle in such manner that the circulating pump and the nozzle together with the associated pipework form a closed path, connecting a small supply of disinfectant solution to said closed path and circulating the disinfectant solution around the closed path during a disinfection period in order to disinfect the pump, nozzle and associated pipework.

2. A method according to claim 1, wherein said closed path includes air supply pipework associated with the nozzle, whereby the air supply pipework and air channels or ports in the nozzle are simultaneously disinfected.

3. A method according to claim 1, wherein the water circulating system comprises a plurality of nozzles which are blanked off or capped so that said closed path is a series/parallel arrangement with each parallel branch therefore including a corresponding one of the nozzles.

4. A method to claim 1, wherein the used disinfectant is discharged direct to drain at the end of the disinfection period.

5. A method according to claim 1, wherein the used disinfectant is discharged into the tub itself for disinfection of the latter at the end of said disinfection period.

6. A method according to claim 5, wherein the used disinfectant is discharged through a flexible hose to a hand-held brush and the latter is used to clean out the bath tub.

7. A whirlpool bathtub comprising:
a tub having at least one nozzle mounted therein;
means for capping off said nozzle;
pipework forming a closed loop, with, and connecting to, said nozzle, a circulating pump, and a valve on a reservoir of disinfectant solution, when said capping means caps off said nozzle.

8. A whirlpool bath tub installation including a bath tub according to claim 7 and wherein the installation comprises a disinfectant supply tank and a circulating pump connected to said nozzle through water supply pipework, and the tub has adjacent the nozzle an outlet connectable to a suction inlet of the pump and through which in use during bathing recirculated water is drawn by the pump with said capping means being operative to blank off the nozzle and the outlet from the inner space of the bath tub in such manner that during said disinfection period the disinfectant solution in said supply tank circulates through the nozzle and returns to the pump through the adjacent outlet.

9. A whirlpool bath tub installation including a bath tub according to claim 7 and wherein the capping means blank off the nozzle in such manner that associated air supply pipework connected to the nozzle forms part of said closed path and the recirculated disinfectant solution is returned to the pump from the nozzle through the air supply pipework and via the disinfectant supply tank.

10. An installation according to claim 9, wherein the capping means comprise a capping member which closely fits the end of the nozzle.

11. An installation according to claim 9, comprising first valve means which alternatively connect the inlet of the circulating pump to the bath tub or to the supply tank, and second valve means which alternatively connect the air supply pipework to an air suction inlet or to discharge into the supply tank during a disinfection period.

12. An installation according to claim 11, wherein said nozzle is one of a plurality of nozzles connected in parallel to said water supply and air supply pipework.

13. An installation according to claim 11, wherein said first valve means operates to connect the disinfectant supply tank and to discharge used disinfectant solution into a drain or into the bath tub at the end of a disinfection period.

14. An installation according to claim 13, comprising a flexible hose terminating at a hand-held brush and through which the supply tank discharges used disinfectant solution via said first valve means in the bath tub.

15. An installation according to claim 11, wherein said air supply pipework is connected to the air suction inlet through a first check valve of said second valve means and to a pipe which discharges into the supply tank through a second check valve of said second valve means, said check valves being oppositely connected to allow a flow from the suction inlet to said nozzle through the first check valve and air supply pipework when the latter is under suction and the second check valve alternatively allows the air supply pipework to discharge to the disinfectant supply tank when that pipework is under pressure.

16. An installation according to claim 11, wherein said first valve means comprises a plug valve incorporated in a drain outlet of the bath tub with a valve plug which is raised from a seated position to open the drain outlet and which, when in the seated position closing the drain outlet is angularly moveable between two alternative positions in one of which positions it connects the pump inlet to the disinfectant supply tank and in the other of which it connects the pump inlet to the bath tub.

17. The whirlpool bath according to claim 7, wherein said capping means seals off the end of the nozzle with respect to the inner space of the bathtub, when aid capping means is operative.

* * * * *